(12) United States Patent
Brown

(10) Patent No.: US 7,771,390 B2
(45) Date of Patent: Aug. 10, 2010

(54) SYRINGE ADAPTER WITH A DRIVER FOR AGITATION OF THE SYRINGE CONTENT

(75) Inventor: Martin M. Brown, Oslo (NO)

(73) Assignee: GE Healthcare AS, Oslo (NO)

( * ) Notice: Subject to any disclaimer, the term of this patent is extended or adjusted under 35 U.S.C. 154(b) by 0 days.

(21) Appl. No.: 10/523,744

(22) PCT Filed: Aug. 7, 2003

(86) PCT No.: PCT/NO03/00270

§ 371 (c)(1),
(2), (4) Date: Feb. 3, 2005

(87) PCT Pub. No.: WO2004/014533

PCT Pub. Date: Feb. 19, 2004

(65) Prior Publication Data

US 2005/0234337 A1    Oct. 20, 2005

(30) Foreign Application Priority Data

Aug. 7, 2002    (NO) ................................ 20023724

(51) Int. Cl.
*A61M 1/00*    (2006.01)
(52) U.S. Cl. ...................................... 604/151; 604/500
(58) Field of Classification Search ............. 604/82–83, 604/187, 131, 151, 152, 154, 155, 232, 218, 604/500, 506; 600/432; 128/DIG. 1
See application file for complete search history.

(56) References Cited

U.S. PATENT DOCUMENTS 3,993,065 A * 11/1976 Szabo et al. ................. 604/154
4,357,971 A * 11/1982 Friedman ..................... 604/218
4,424,720 A *  1/1984 Bucchianeri ............. 74/424.78
4,529,401 A *  7/1985 Leslie et al. ................. 604/131

(Continued)

FOREIGN PATENT DOCUMENTS

WO            99/27981            6/1999

(Continued)

OTHER PUBLICATIONS

International Search Report for PCT/NO03/00270 dated Jan. 21, 2004.

(Continued)

*Primary Examiner*—Nicholas D Lucchesi
*Assistant Examiner*—Theodore J Stigell
(74) *Attorney, Agent, or Firm*—Robert F. Chrisholm

(57) ABSTRACT

Administration by injection or infusion to patients of an injectable liquid for diagnostic or therapeutic purposes is provided by a syringe adapter connectable with an automatic syringe pump and a syringe containing contents to be dispensed. The syringe adapter includes an adapter body receivable by the syringe pump, a syringe retainer for retaining the syringe, and a syringe driver for agitating the contents of the syringe. More particularly the invention relates to an adapter connectable with a syringe pump and methods for delivery of an injectable liquid using such adapter. By connecting an adapter according to the invention to a syringe and a syringe pump, rotation of the syringe is achieved and homogeneity of the injectable is preserved. Particularly, the injectable liquid is an ultrasound contrast agent comprising an aqueous dispersion of gas-filled microbubbles or of particulate matter.

14 Claims, 10 Drawing Sheets

U.S. PATENT DOCUMENTS

| | | | | |
|---|---|---|---|---|
| 5,240,322 | A | * | 8/1993 | Haber et al. .................. 366/130 |
| 5,647,851 | A | * | 7/1997 | Pokras ........................ 604/131 |
| 6,575,930 | B1 | * | 6/2003 | Trombley et al. ............. 604/82 |
| 6,821,013 | B2 | * | 11/2004 | Reilly et al. ............. 366/162.3 |
| 2002/0077588 | A1 | * | 6/2002 | Schneider et al. ............. 604/82 |
| 2003/0185096 | A1 | * | 10/2003 | Hollstein et al. ............ 366/273 |

FOREIGN PATENT DOCUMENTS

| | | |
|---|---|---|
| WO | 00/12157 | 3/2000 |
| WO | 00/12158 | 3/2000 |
| WO | 00/53242 | 9/2000 |
| WO | 03/053554 | 7/2003 |
| WO | WO 03/053554 A1 * | 7/2003 |

OTHER PUBLICATIONS

International Preliminary Examination Report for PCT/NO0300270 dated Apr. 2004.

* cited by examiner

SYRINGE ADAPTER WITH A DRIVER FOR AGITATION OF THE SYRINGE CONTENT

This application is a filing under 35 U.S.C. 371 of international application number PCT/NO2003/000270, filed Aug. 7, 2003, which claims priority to application number 20023724 filed Aug. 7, 2002, in Norway the entire disclosure of which is hereby incorporated by reference.

FIELD OF THE INVENTION

The present invention relates to devices for administration by injection or infusion of liquid compositions for diagnostic or therapeutic purposes. More particularly the present invention is directed to an adapter for a syringe pump used to dispense the contents of a syringe maintaining a homogeneous solution during dispensing.

DESCRIPTION OF RELATED ART

In a number of medical procedures, it Is desirable to continuously inject a multi-component medium to a patient. An example of such a medical procedure is ultrasound imaging. For ultrasound imaging the most common contrast media comprises gas-containing microbubbles dispersed in an aqueous carrier. A problem with the continuous infusion of such contrast media arises from the tendency of microbubbles to float, since this may lead to inhomogeneities forming within vessels such as power-driven syringes which may be used to administer the contrast agent. This may, for example, lead to an increase in microbubble concentration in the upper part of such a vessel and/or to changes in size distribution occurring at various points within the vessel as larger microbubbles float more rapidly than smaller microbubbles.

Power injectors for continuous controllable delivering of diagnostic and therapeutic injectable liquids are well known. Typically such apparatus include an automatic syringe pump for coupling to a syringe containing an injectable liquid. Such syringe further has a plunger or piston movable within the barrel of the syringe to expel the liquid through a tip thereof. The automatic syringe pump typically has a syringe-receiving unit, adapted to hold the syringe, and an electromechanical arrangement organized to push the plunger of the syringe at a desired rate. The mode and rate of injection or infusion is hence accurately controlled. Compared to hand injection, automatic syringe pumps have the benefit of maintaining a consistent flow over a long time, thereby providing a consistent amount of the injectable liquid, such as a contrast media, In the blood stream.

The available syringe pumps on the market have, however, no control of the homogeneity of the injectable liquid stored in the syringe barrel during the course of administration. When the injectable liquid is a dispersion of particles that tend to settle, float, coalesce or segregate, such as e.g. an ultrasound contrast agent, it is desirable to keep the contents of the syringe homogeneous during administration. As automatic syringe pumps are frequently used in infusion or injections, and as such equipment is available in most hospitals, it is also desirable to enable use of such pumps for administration of an injectable liquid wherein preservation of homogeneity is needed. The present method and devices give an effective solution to this problem.

Some methods and devices for maintaining a homogeneous solution during administration have been described earlier. WO 99/27981 describes an automatic injection system and a method for its use. The injection system includes a syringe containing a dispersion and this dispersion is subjected to a rotation or rocking motion in order to maintain a homogeneous dispersion. This patent application further describes an injection system comprising a syringe, automatic electromechanical power means, and means for agitating the dispersion in the syringe, such as e.g. a set of rollers. The injection system includes a pump suited for rotation of an integrated syringe.

WO 00/53242 describes devices, systems and methods for dispensing a multi-component medium. A system described comprises a container to hold the medium, a pressurizing device, such as a pump, and an agitation mechanism or device to maintain the components of the medium in a mixed state. Several ways of achieving agitation are described, e.g. rotation of a storage volume.

WO 00/12157 and WO 00/12158 describe syringes and pumps incorporating an agitation device, such as a ball, respectively a magnetic agitation device and a mechanical agitation device. WO 00/12158 further describes that the system can include accessories encompassing devices physically connected to a pump and assume the role of moving the entire pump or parts thereof in such a way that the syringe changes position. Examples of such accessories are a table for the pump executing a wobbling movement and a motor-drive shaft.

Each of the above-described systems therefore provide agitation means integrated into the syringe pump or a syringe. There is still a need in the art, however, for providing an agitation capability to a linear-stroke automatic syringe pump both before and during administration of the injectable liquid.

SUMMARY OF THE INVENTION

In view of the needs of the art the present invention provides a syringe adapter connectable with an automatic syringe pump and a syringe containing an injectable liquid to be dispensed. The adapter comprises means for agitating the injectable liquid of the syringe.

A syringe is defined as a unit that may contain a liquid composition for injection or infusion. The syringe mainly comprises a barrel, a nozzle and a plunger. The term syringe also encompasses so called cartridges adapted to be connected to syringe pumps. Such cartridges include a plunger, but not necessarily a plunger rod.

A syringe pump is defined as an apparatus used in automatic and controlled administration of a liquid composition from a syringe. Such pumps are also called infusion pumps, power injectors and injector systems.

Furthermore, the present invention provides apparatus and methods for delivery of an injectable liquid, such as an ultrasound contrast agent, to a patient. Particularly the invention provides methods and devices for securing homogeneity of the liquid during administration, such as during an infusion procedure. The invention gives a method and means whereby the injectable liquid is kept under sufficient agitation so as particles in the composition do not settle, segregate, float or agglomerate undesirably.

In the present invention the mixing device is an adapter which receives a syringe. The adapter itself is received by an automatic syringe pump. The adapter of the present invention is suitable for use with available marketed pumps and with conventional syringes so as to preserve the homogeneity of the liquid to be administered. The great advantage of the adapter of the invention is that this allows for use of standard syringe pumps available at the market. Additionally it is easy to use and validate.

By connecting the adapter to a pump and a syringe, rotation of the syringe is achieved and the composition in the syringe is sufficiently agitated to keep the components of the injectable liquid in a mixed state during administration. Mechanical agitation is provided to the extent that is sufficient to keep the composition homogeneous but insufficient to break or damage the particles in the composition.

DETAILED DESCRIPTION OF THE INVENTION

Figure 1:
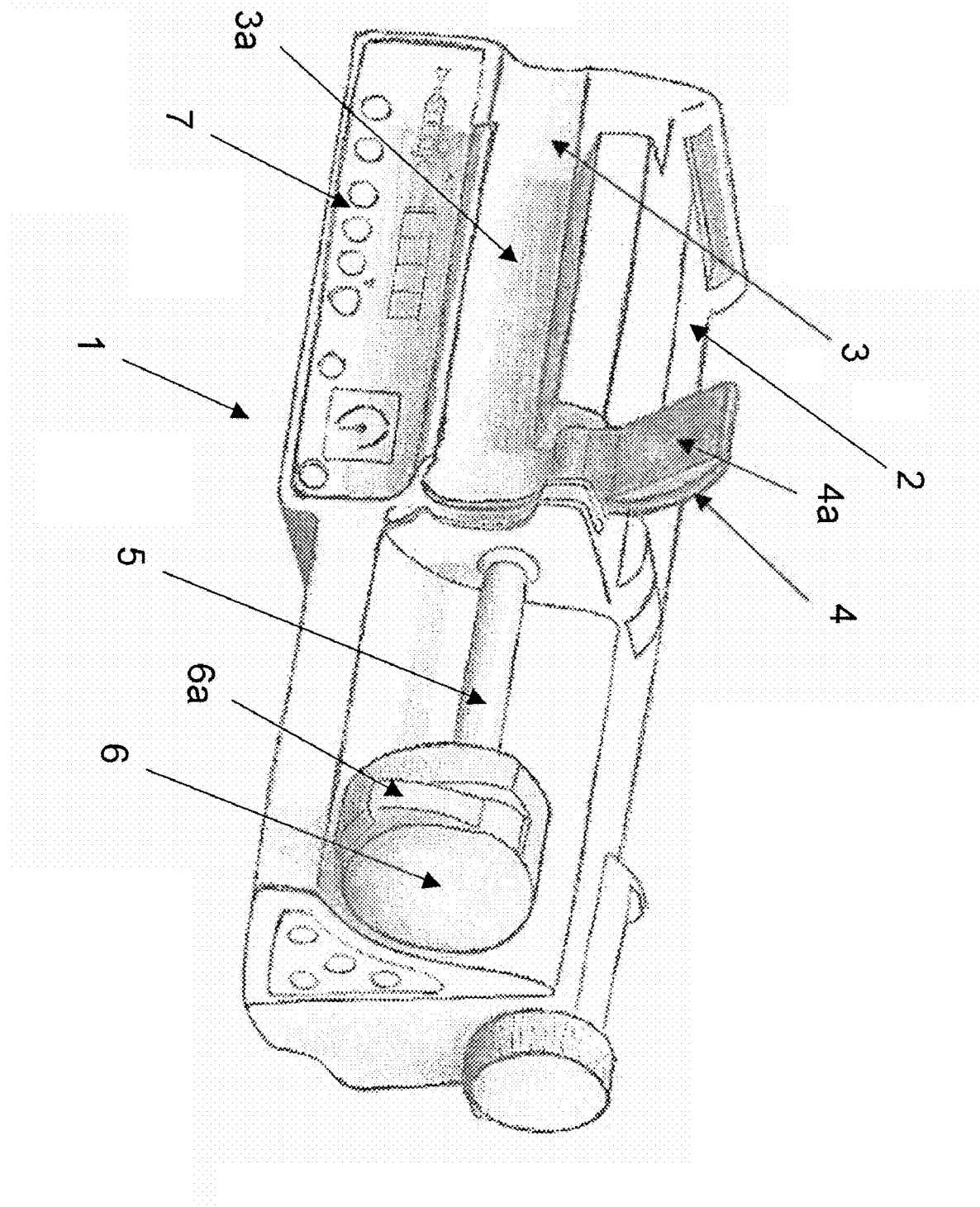
FIG. 1 illustrates an automatic syringe pump of the prior art.

A first embodiment of the present invention is an adapter connectable with an automatic syringe pump and/or a syringe, the syringe containing contents to be dispensed, said adapter comprising means for agitating the content of the syringe.

The adapter is detachably connectable to standard syringe pumps and syringes. That is, the adapter can be connected, joined, linked, fastened or coupled to, and de-tached from, an automatic syringe pump and/or a syringe. The adapter comprises an adapter body receivable by a syringe-receiving unit of the syringe pump. The adapter further comprises means for agitating the syringe by primary rotational movements.

Various types of syringe pumps are currently available on the marked. Briefly stated, such pumps generally comprise a syringe receiving-unit, a dispense shaft or drive head, a motor and electronics to drive the dispense shaft controllably against a syringe plunger or piston, and a control keyboard. Many pumps also have a size-reading unit or in another way has the capability of reading the size of the syringe attached. When placing a syringe in the syringe receiving-unit of the pump this size-reading-unit registers the diameter of the syringe placed in the pump. Based on this size-reading the syringe dimensions are calculated giving the correct injection rate when set to operate. The pumps are designed to comply with standard syringe sizes.

To ensure compatibility with existing pumps the adapter of the invention includes a portion having the same or similar geometry as a syringe. The adapter is designed to have partly the same geometry as a syringe in order to comply with the syringe receiving-unit, e.g. a syringe cradle, of the pump. Desirably the adapter also has geometry complying with any size-reading-unit of the pump. When placing the adapter in the syringe-receiving-unit of the pump and the syringe size-reading-unit is closed the pump will select the correct syringe size, based on the reading of the adapter dimensions, and thereby giving the correct injection rates when set to operate.

The adapter at least comprises an adapter body, a syringe retainer, and a syringe driver for agitating the injectable contents of the syringe.

To ensure compliance with the pump the adapter body comprises desirably an elongate cylindrically shaped housing portion receivable in the syringe pump. Desirably, this body has a circular cross-section, resembling the barrel of a syringe. Most desirably, to ensure maximum compatibility with existing pumps used in hospitals the adapter has at least partly the same shape and size as a 50-ml syringe. When the adapter is placed in a pump, the pump therefore "believes" a syringe has been placed in the pump, and it calculates the right rate of administration, based on the dimensions of the adapter. A size readable-unit of the adapter is designed to comply with any size-reading-unit of the pump. This unit desirably has substantially the same cross-section as the barrel of the syringe to be used. Most desirably the size-readable unit of the adapter has the diameter as the barrel of a 20-ml or 10-ml syringe.

The syringe driver comprises means for agitating the content of the syringe. Desirebly the adapter body further includes such means for providing rotation of the syringe retainer. These means for rotation could comprise a motor, electronics, means for communicating with the user (display, buttons etc.) and converters. A power source like batteries, optionally chargeable, mains to the net, or a mechanical energy source may be included. Rotation can be achieved e.g. with a belt or wheel actuated by a motor of some kind. The motor is desirably integrated inside the adapter body. Optionally, any size-readable unit can either be integrated as part of the adapter housing or could be a separate unit connected with the housing.

The syringe retainer of the adapter is designed to hold and rotate the syringe. Energy is transferred from the motor in the adapter body to the syringe retainer and motor driven rotation of the syringe is enabled. There may hence be a torsion energy transfer from the motor to the syringe retainer. The rotational part of the retainer may comprise a swivel connector, a ball-bearing rotating arrangement that allows rotating while being fixed, a needle bearing system, a sleeve bearing system, rolling bearings or others, and holding means such as jaws or a clamp. The syringe retainer comprises both holding and rotational means. The syringe retainer may include a snap/quick fit system, a splint, barbs, threaded connections or other locking mechanisms for connecting the syringe to the adapter. Preferably the syringe retainer includes an insertion aperture, through which a syringe may be threaded. The retainer should then comprise a syringe ring which further comprises syringe retaining means extending about the insertion aperture for engaging and retaining the syringe. Moreover, the syringe retainer may be designed to accommodate the flanges of a syringe to form a lockable rotateable holder. A syringe may then be inserted by threading it through the insertion aperture of the adapter, rotating the syringe 90 degrees and reversing the direction of insertion. The flanges of the syringe will then engage the rotating part of the adapter. Alternatively, the syringe may be threaded through the insertion aperture and locked directly in the retaining means without having to rotate it 90 degrees. The syringe retainer will then engage and retain the syringe after direct insertion of the syringe. The attachment of a guide piston, as later described, will also support holding the syringe in place in the syringe retainer. The syringe ring is preferably exchangeable.

The syringe driver means enables agitation of the content of the syringe. The syringe driver preferably comprises a motor and drive means, preferably positioned within the adapter body as described above. The drive means, transferring power from the motor to the syringe, may e.g. comprise drive belts, toothed wheels, axles, shafts, chains or straps. Preferably the drive means comprises a drive belt engaging a moving portion of the motor and the syringe retainer, such as the syringe ring in the insertion aperture of the syringe retainer. The syringe driver causes the syringe ring to reciprocally rotate about the insertion aperture.

A further aspect of the invention is a plunger-pressure-unit of the adapter which is designed to transfer the injection movement from the drive head of the pump to the plunger of a syringe held by the syringe retainer. The dispense shaft of the pump can hence act on this plunger-pressure-unit, to effect movement of the pump to the syringe plunger. The plunger-pressure-unit hence acts as an extension to the drive head. The plunger-pressure-unit may simply consist of a guide piston. The drive head of the pump may hence act directly on this guide piston transferring movement from the pump to a syringe plunger. The adapter body then defines a guide piston opening and an elongate guide piston passageway in fluid communication with the guided piston opening for slidably receiving the guide piston between a first and second position. However, the geometry and dimensions of some drive heads may be sufficient to directly act upon a plunger of the syringe held by an adapter of the present invention, making such plunger-pressure-unit redundant. Alternatively, the plunger-pressure-unit may comprise an extension arm in addition to the guide piston. The extension arm preferably includes a free end in movable spaced registry with the syringe retainer. Preferably, the extension arm is pivotally mounted to the guide piston. Further, the extension arm may support a dispense rod for engaging the syringe plunger. Ideally, the dispense rod should be able to either rotate freely or with as little friction as possible with the syringe plunger. Preferably, the guide piston is adopted to move slideably, with as little friction as possible.

The different parts of the adapter may be arranged in alternative ways. The adapter body, the syringe retainer, and the guide piston may all be positioned substantially in-line. When in-line, desirably the adapter is shaped as a syringe having a substantially elongate cylindrically shaped housing, a guide piston extending from one end of the housing, going generally through the cylindrical housing, and a syringe retainer, forming the other end of the cylindrical. A syringe can hence be mounted to one end of the elongate body. When placing a syringe in the retainer the cylindrical housing, the guide piston and the syringe will be positioned substantially in-line. Alternatively, the adapter is designed such that the syringe retainer holds the syringe substantially in parallel with the cylindrical housing. Preferably, the syringe retainer is offset from the adapter body.

A syringe placed in the adapter is subjected to a rotational agitation, continuous or discontinuous, optionally altering the rotation direction and desirably the speed of the rotation. Generally, when a syringe containing a stationary fluid is rotated a certain angle around its central longitudinal axis, the fluid volume inside is displaced in a predictable manner. When the motion is reversed by moving the cylinder back to its original angular position, the fluid will eventually also move back again to its original position, and sufficient agitation has not been achieved. The adapter of the invention desirably imparts a rotation around the longitudinal central axis of the syringe. The rotation may however also take place outside the central axis, turning the syringe around a line outside the central longitudinal axis. The movement may also take place in the longitudinal direction of the syringe.

The movement may be continuous or discontinuous. However, the adapter desirably subjects the syringe to an oscillating rotation making an asymmetric pattern. The oscillating rotation may be performed by alternately rotating the syringe at a certain angle in one direction and then reciprocally in the opposite direction so as to prevent a harmonic oscillation of the dispensable fluid. Alternatively, the syringe may be rotated at different angles in the opposite directions. The most preferable way of achieving an asymmetric rotation is by alternately rotate the syringe in opposite directions, around its longitudinal central axis, wherein the speed of rotation differs in the two directions. Alternatively, asymmetric rotation may be achieved by rotating at set angles but at varying speed of rotation. If the angular speed of rotation is different when the reverse rotation is performed, there will be a small net displacement of the fluid when returning to the original position. This is caused by non-linearities in the viscous behavior of the fluid, and possibly also turbulence if the angular acceleration is high enough. An oscillating rotational shaking of a syringe in this manner will hence cause a long-term net rotation of the fluid inside the syringe. A short angle back-and-forth rotational shaking has a substantial advantage, since any tubing from the syringe to the patient will not become twisted. Although the angular excursions might be quite small, there will be a complete shaking, since a continuous circulation flow pattern is generated in the syringe. About 1-6 rotations should however not be a problem for the tube.

FIG. 1 illustrates an automatic syringe pump 1 of the prior art. Similar pumps are available on the market, such as for instance a Fresenius DPSIS. A syringe with a composition for delivery may be connected to or placed in the pump, and the pump enables controllable delivery of the compositions to a patient. An adapter of the invention may be used with such pump. The pump of FIG. 1 has a pump housing 2. The pump further has a syringe-receiving-unit 3. This unit is designed to receive a syringe, and will typically have a substantially half-cylindrical shape, forming a cradle 3a. In combination with the syringe-receiving-unit 3 there is a syringe size-reading-unit 4. When placing a syringe in the syringe receiving-unit 3 this part of the pump reads the size of the syringe installed, usually based on the diameter of the syringe. The size-reading-unit 4 will typically comprise a clasp 4a that can pivot between an opened position allowing access to cradle 3a and a closed position in spaced registry with cradle 3a so as to retain a syringe therein. The pump further comprises an elongate longitudinally-displaceable dispense shaft 5. When placing a syringe in the pump the dispense shaft 5 engages and moves the plunger rod of the syringe. The housing 2 includes electromechanical arrangement enabling a driving of the dispense arm 5 of the pump towards the syringe at a desired rate so as to provide controlled dispensing of the contents of the syringe. The dispense arm 5 supports a pump drive head 6 at one end which itself may support drive release and anti-siphon controls 6a. Drive head 6 engages the piston shaft of a common syringe or dispense syringe positioned in cradle 3a so as to cause the contents of the syringe to dispense as dispense arm 5 carries drive head 6 towards the syringe. The pump should further have a control panel 7 for assisting an operator.

Figure 2A:
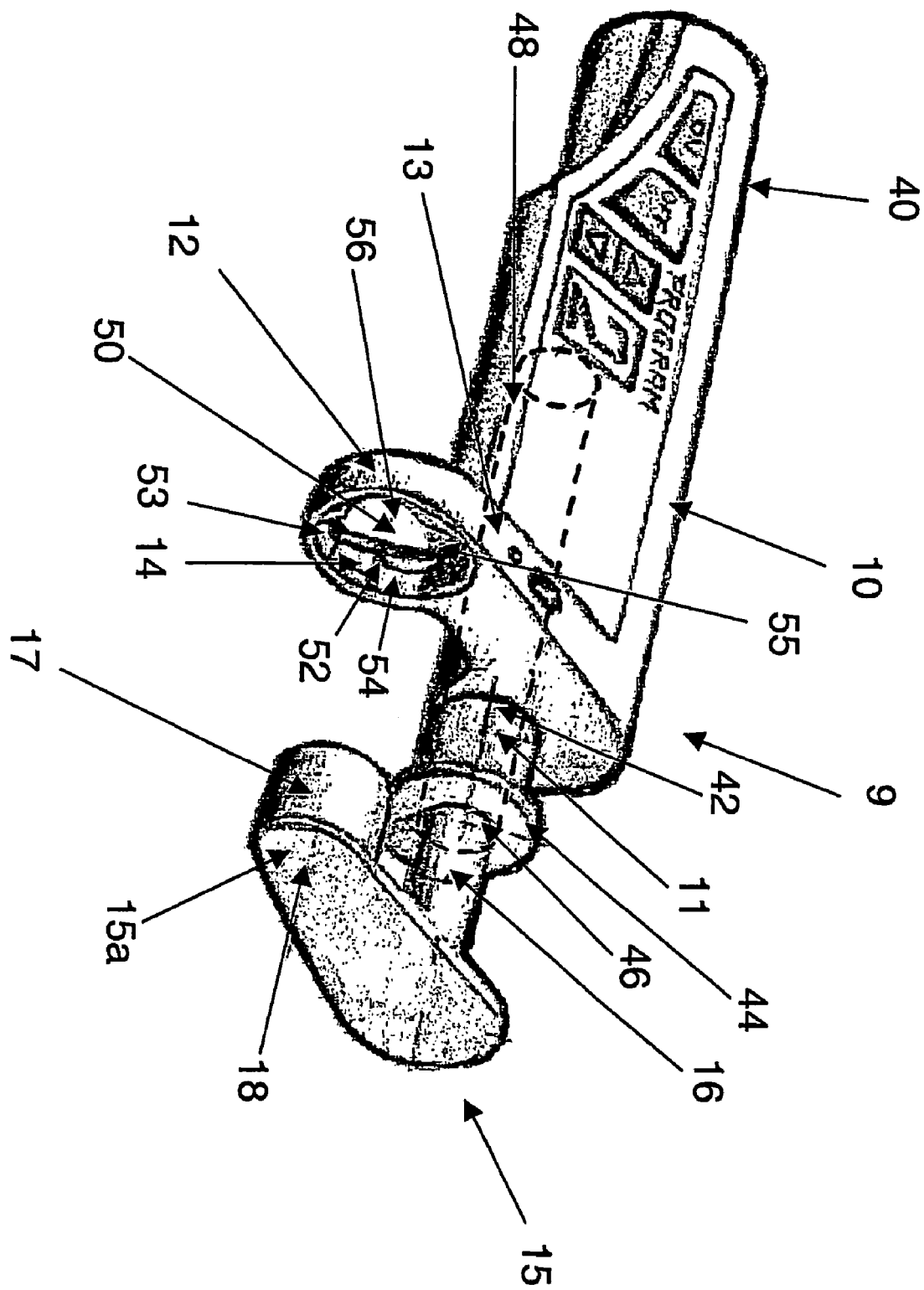
FIG. 2a illustrates a first adapter according to the present invention.

FIG. 2a illustrates a first example of an adapter 9 according to the present invention. The adapter 9 is compatible with the pump 1 of FIG. 1. The adapter 9 includes an elongate adapter body, or housing, 10 having geometry complying with the syringe receiving-unit 3 of the pump 1 in FIG. 1. Adapter 9 also includes a syringe retainer 12 for retentively engaging a syringe having contents to be dispensed. A syringe driver mechanism is also provided, described hereinbelow, for agitating the contents of the syringe. Housing 10 is typically formed of a suitably rigid plastic material and desirably includes a substantially elongated cylindrical portion 40, resembling the barrel of a syringe. Housing 10 includes a size readable-unit 11 designed to fit within the size-reading-unit 4 of the pump 1. Size readable-unit 11 comprises a neck 42 and an annular shoulder 44 which simulate the size and shape of the base end of a syringe or dispense syringe.

Figure 4:
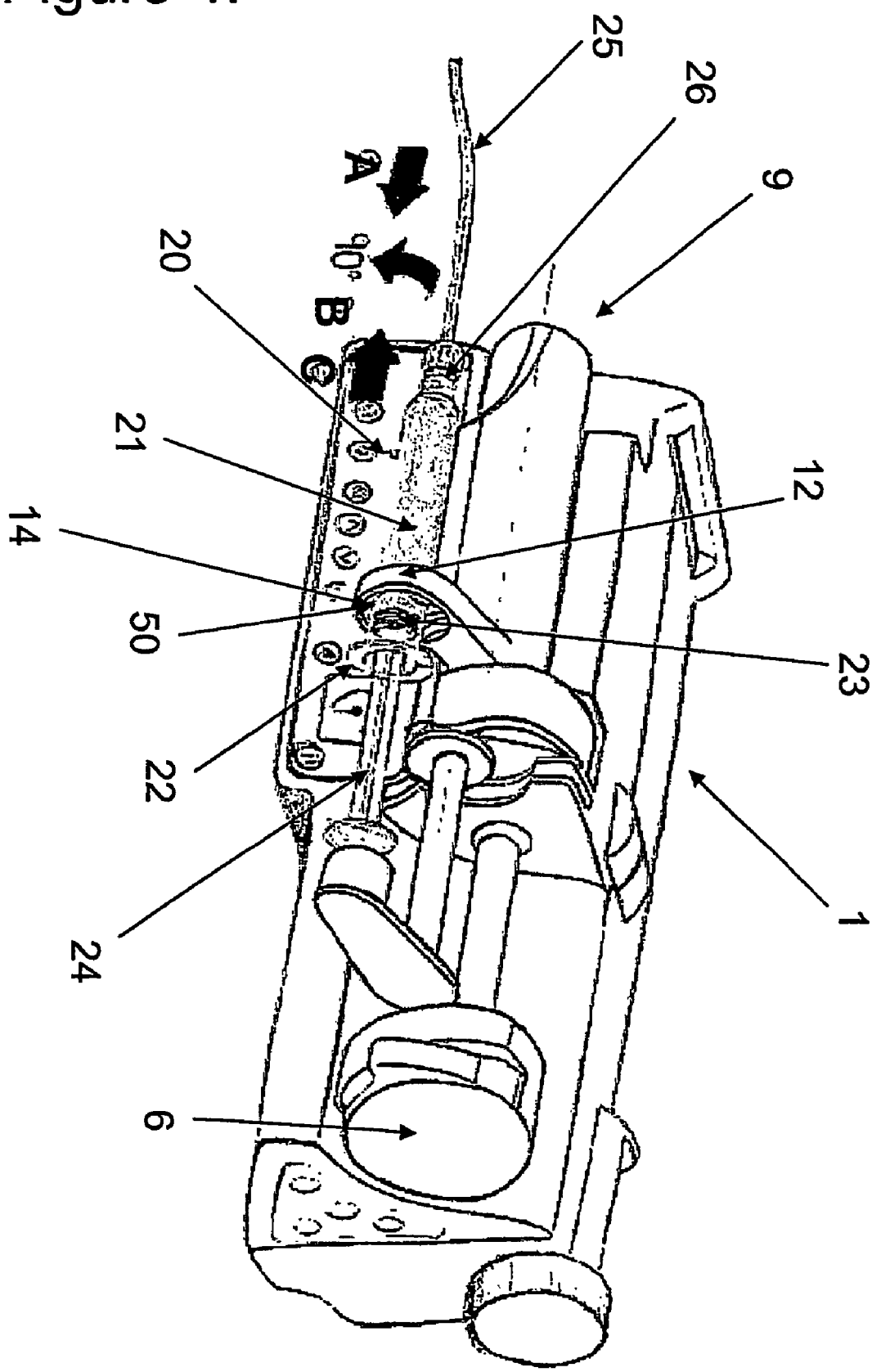
FIGS. 4 and 5 illustrate the adapter of FIG. 2 placed in an automatic syringe pump and how to connect the adapter to a syringe.

Adapter 9 further includes a syringe retainer 12 at a free end of a holding arm 13 extending substantially transversely to housing 10. Syringe retainer 12 defines an annular track within which a syringe ring 14 may rotate. A syringe may be positioned in syringe retainer 12 and rotated with syringe ring 14, as shown in FIG. 4. Syringe ring 14 defines an insertion aperture 50 into which a syringe having contents to be dispensed may be inserted and retained. Syringe ring 14 desirably includes a number of retaining arms 52 extending towards insertion aperture 50 for retentively engaging an inserted syringe. Retaining arms 52 define opposed first and second open notches 53 and 55 for allowing the flanges of a syringe to pass there through. Retaining arms 52 further define there between opposed first and second closed flange-receiving notches 54 and 56 into which the flanges of a syringe may be retentively engaged.

Annular shoulder 44 defines a guide opening 46 in fluid communication with a guide piston passageway 48, shown by phantom lines, defined by housing 10. Passageway 48 slidingly accommodates a guide piston 16 therein. A free end of guide piston 16 supports an extension arm 15 which engages the drive head 6 of syringe pump 1. Extension arm 15 extends substantially transversely to guide piston 16 and desirably supports a dispense rod 17 at a free end 15a in spaced registry with insertion aperture 50. Dispense rod 17 may be rotationally supported on extension arm 15 by an axle 18. Alternatively, dispense rod may be fixed with respect to extension arm 15. Movement of extension arm 15 and guide piston 16 is further illustrated in FIG. 5.

Figure 2B:
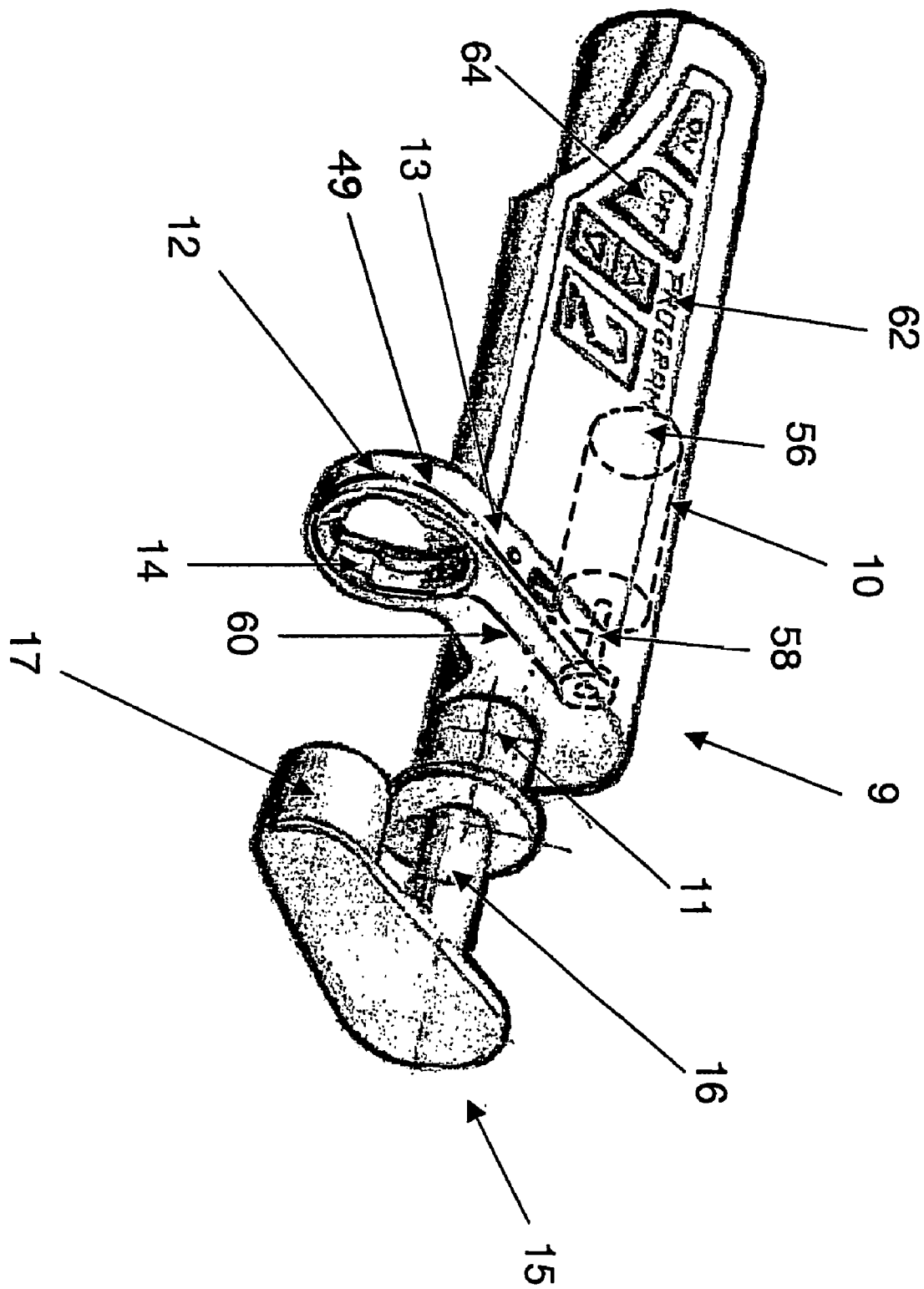
FIG. 2b illustrates the adapter of FIG. 2a further indicating the syringe driver.

The adapter 9 further includes means for imparting rotational energy to the syringe ring 14, as shown by phantom lines in FIG. 2b. Adapter 9 includes an electric motor 56 which rotates a drive shaft 58. One free end of drive shaft supports a drive belt 60. Drive belt 60 extends through an open interior portion of holder 13 and in annular track 49 about syringe ring 14. Motor 56 may rotate continuously in a single direction as well as in a reciprocating motion so as to causes a syringe held by syringe retainer 12 to be agitated, thereby preserving the homogeneity of the contents of the syringe. Motor 56 desirably urges syringe ring 14 to reciprocatingly rotate through about ninety degree arcs so as to impart a reciprocating rotation of the inserted syringe. Motion of motor 56 is desirably directed by controller circuitry 62 which operates according to operator selected inputs at control panel 64. Control panel 64 desirably provides an operator to, at a minimum, select a pre-programmed routine for rotation of syringe ring 14, such as the speed, direction, and amount of rotation. On-off controls allow the operator to commence and terminate agitation of the inserted syringe.

Figure 3:
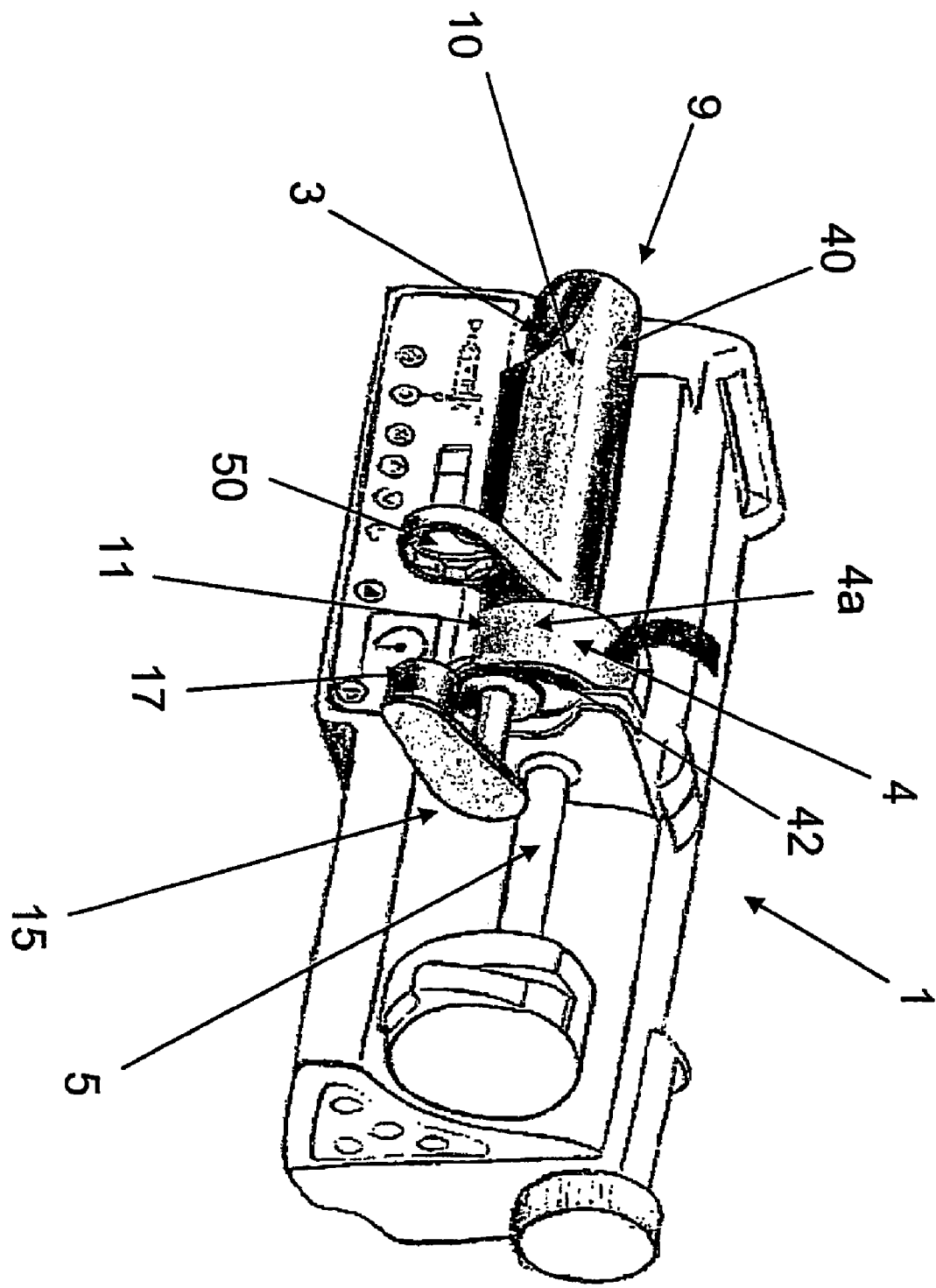
FIG. 3 illustrates the adapter of FIG. 2 placed in the automatic syringe pump of FIG. 1.

FIG. 3 illustrates the adapter 9 of FIG. 2 placed in the automatic syringe pump 1 of FIG. 1. Cylindrical portion 40 of housing 10 of the adapter is positioned in cradle 3a of syringe receiving-unit 3. Extension arm 15 and dispense rod 17 are shown positioned towards the insertion aperture 50 of adapter 9. When having positioned the adapter 9 in the syringe receiving-unit 3, the clasp 4a of size-reading-unit 4 is in the closed position about neck 42 of size readable unit 11. The pump may correlate the outer dimensions of neck 42 with a stored software program, thereby giving the correct injection rates when set to operate.

FIG. 4 illustrates the adapter 9 positioned in an pump 1 while also accommodating a syringe 20. Syringe 20 is a typical syringe as known in the art and includes an elongate barrel 21, flanges 22 transversely-extending from a base of barrel 21, a plunger 23, and a plunger rod 24. Syringe 20 is optionally connected to a tubing 25 at the syringe nozzle 26. The filled syringe 20 is inserted, plunger end first (as shown by arrow A), through insertion aperture 50 of syringe ring 14 desirably. The syringe ring 14 of syringe retainer 12 defines a pattern complying with the flanges 22 of the syringe to allow the flanges to clear through aperture 50. After having Inserted syringe 20 through syringe ring 14, the syringe 20 is rotated 90 degrees (depicted by arrow B) and the direction of insertion is reversed (depicted by arrow C) to retain syringe 20 within syringe ring 14. The flanges 22 of the syringe will engage with the retaining arms 52 of syringe ring 14 thereby locking syringe 20 in the syringe retainer 12. The syringe 20 now extends generally in parallel to adapter housing 10.

Figure 5:
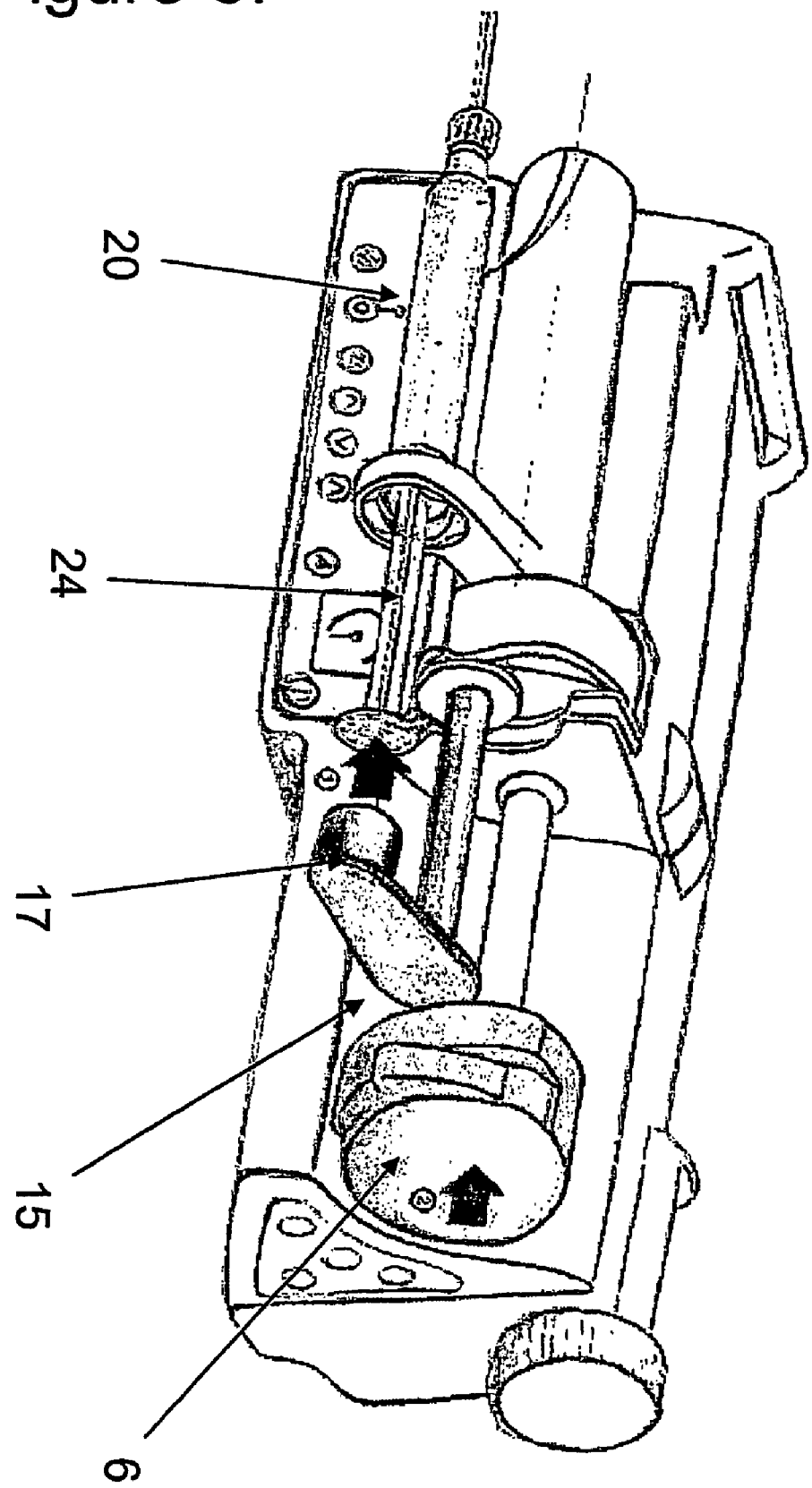
Figure 6:
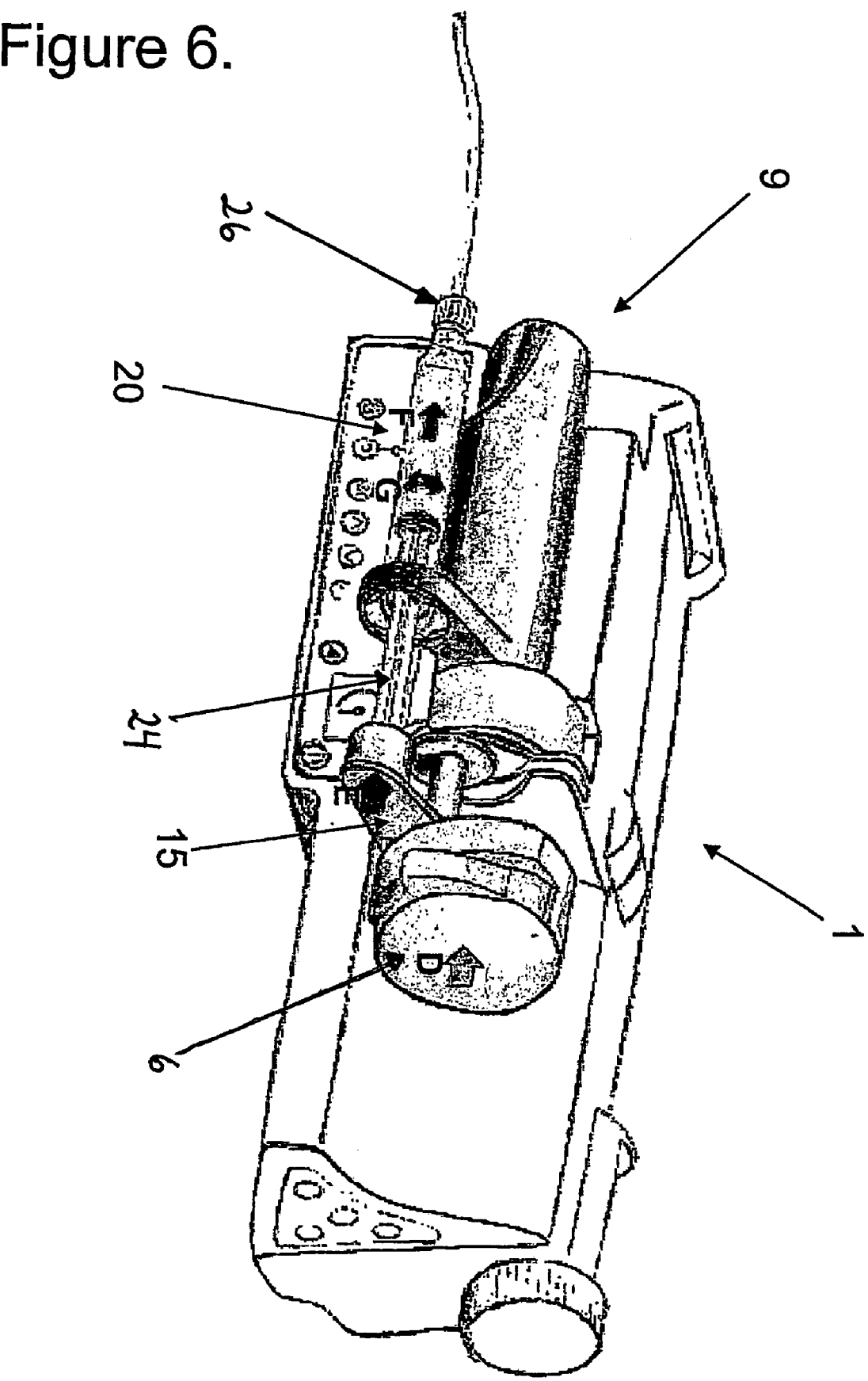
FIG. 6 illustrates the operation of an apparatus comprising a pump, a syringe and an adapter of FIG. 2.

FIG. 5 further illustrates the cooperation between drive head 6 of the syringe pump, extension arm 15 of the adapter, and syringe plunger rod 24 so as to dispense the contents of syringe 20. The dispense rod 17 of extension arm 15 may be manually positioned in abutting engagement with the free end of plunger rod 24 of syringe 20. Pump drive head 6 is moved into abutting engagement with extension arm 15. The entire dispense apparatus, comprising pump 1, syringe 20, and adapter 9 is now ready for operation, as is further illustrated in FIG. 6. Movement of drive head 6 urges extension arm 15 and, hence, plunger rod 24 in a dispensing direction which discharges the contents of syringe 20 through nozzle 26. Pump 1 may be set to run with injection rates as per instructions for the product to be injected or infused. As pump 1 cannot distinguish between adapter 9 and syringe 20, all features, such as alarms, occlusion stop etc. in the pump will still be active. During injection syringe 20 will have the set longitudinal dispense rate (denoted by arrows D,E, and F) ensured by the pump 1, while the optimum sequence of alternating rotation (denoted by arrow G) of the syringe 20 is ensured by adapter 9.

Figure 7:
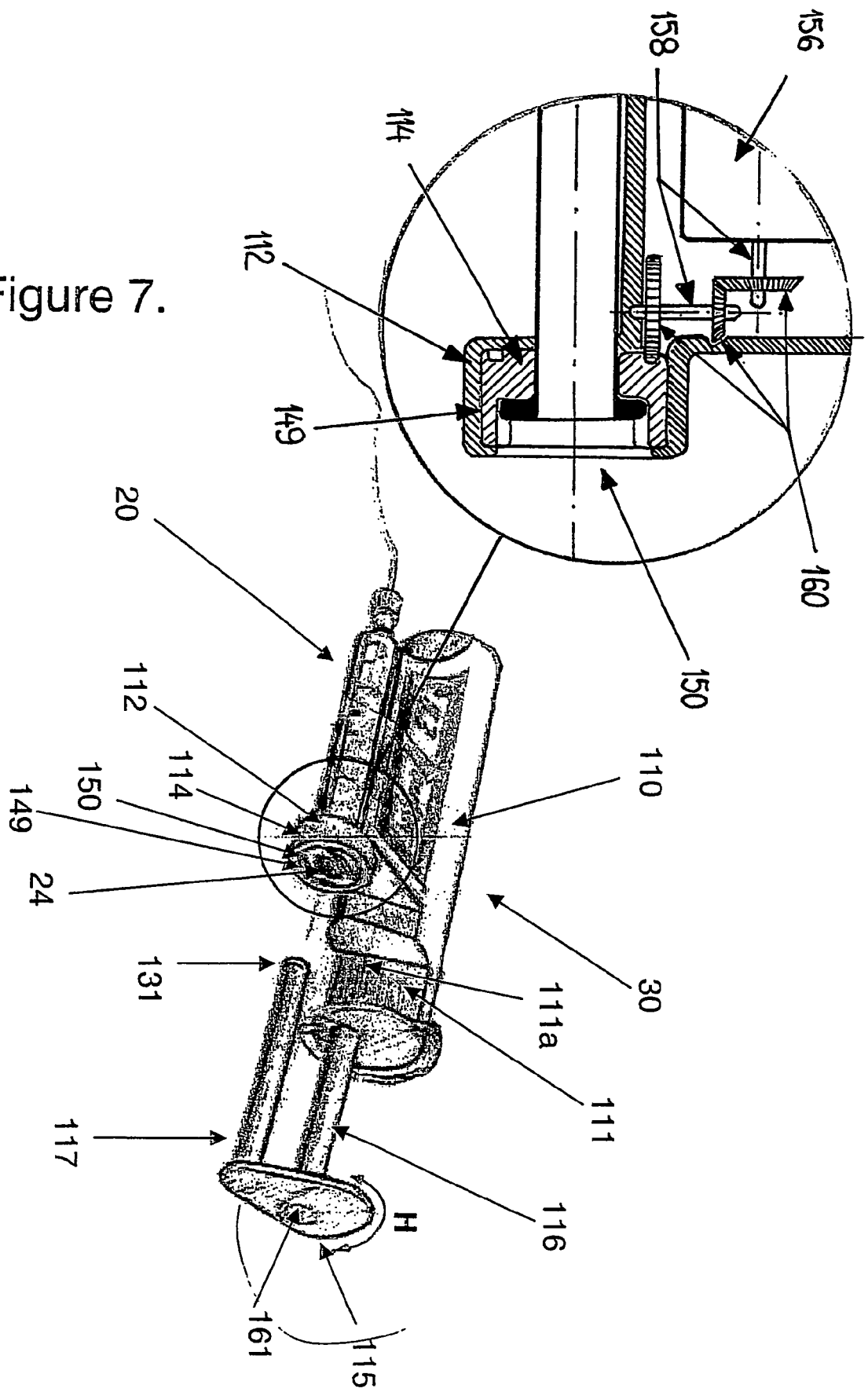
FIG. 7 illustrates a second embodiment of an adapter according to the present invention.

FIG. 7 illustrates a second alternative of an adapter 30 according to the invention connected to a syringe 20. This adapter 30 has the same main parts as the adapter 9 of FIG. 2, with like numerals denoting like components; a housing 110, a syringe size readable-unit 111, an extension arm 115 and a syringe retainer 112. In this alternative, however, syringe size readable-unit 111 forms an integrated part of the housing 110. Desirably, syringe size readable-unit 111 includes a substantially circular cross-section but it may include a substantially planar portion 111a so as to provide an outer dimension shaped to mimic the dimensions of a particular-sized syringe to the size-reading-unit 4 of pump 1. Further, syringe retainer 112 is directly mounted to housing 110, without an extending holder arm. The extension arm 115 is supported by elongate guide piston 116 and supports dispense rod 117. Member 117 is an elongate member especially suited for dispensing the contents from dispense syringes which, while including a slidable piston, lack a plunger rod. Member 117 thereby acts as the plunger rod to move the slidable piston. Dispense rod 117 further supports a swivel 131 at a free end thereof in spaced registry with insertion aperture 150. Swivel 131 allows the plunger rod 24 of a syringe 20 to more freely rotate with syringe barrel 21. The present invention contemplates that extension arm 115 may be pivotally mounted at an axle 161 so as allow dispense rod to be movable about arrow H between opposed positions in and out of registry with insertion aperture 150. Axle 161 thereby allows a syringe to be loaded through insertion aperture 150 nozzle end first. A more detailed sketch of the retainer 112 is shown in a separate extract in FIG. 7. An electric motor 156 is in connection with a rotating shaft 158 In driving engagement of a syringe ring 114. Syringe ring 114 rotates within an annular track 149 defined by syringe retainer 112. The syringe ring 114 and the drive shafts 158 are connected by several toothed wheels 160 to enhance driving engagement therebetween.

Figure 8:
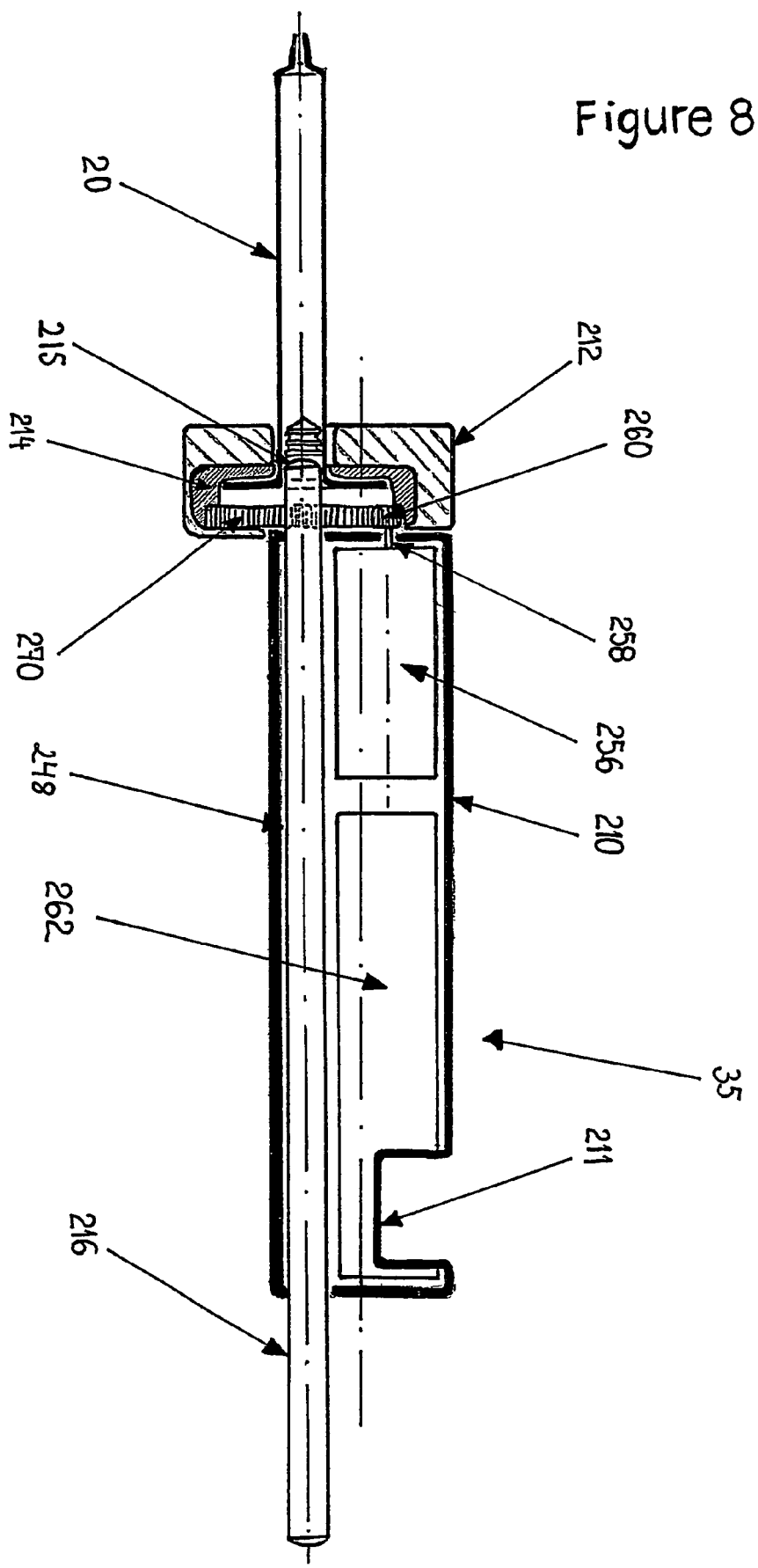
FIG. 8 illustrates a third embodiment of an adapter according to the present invention.
Figure 9:
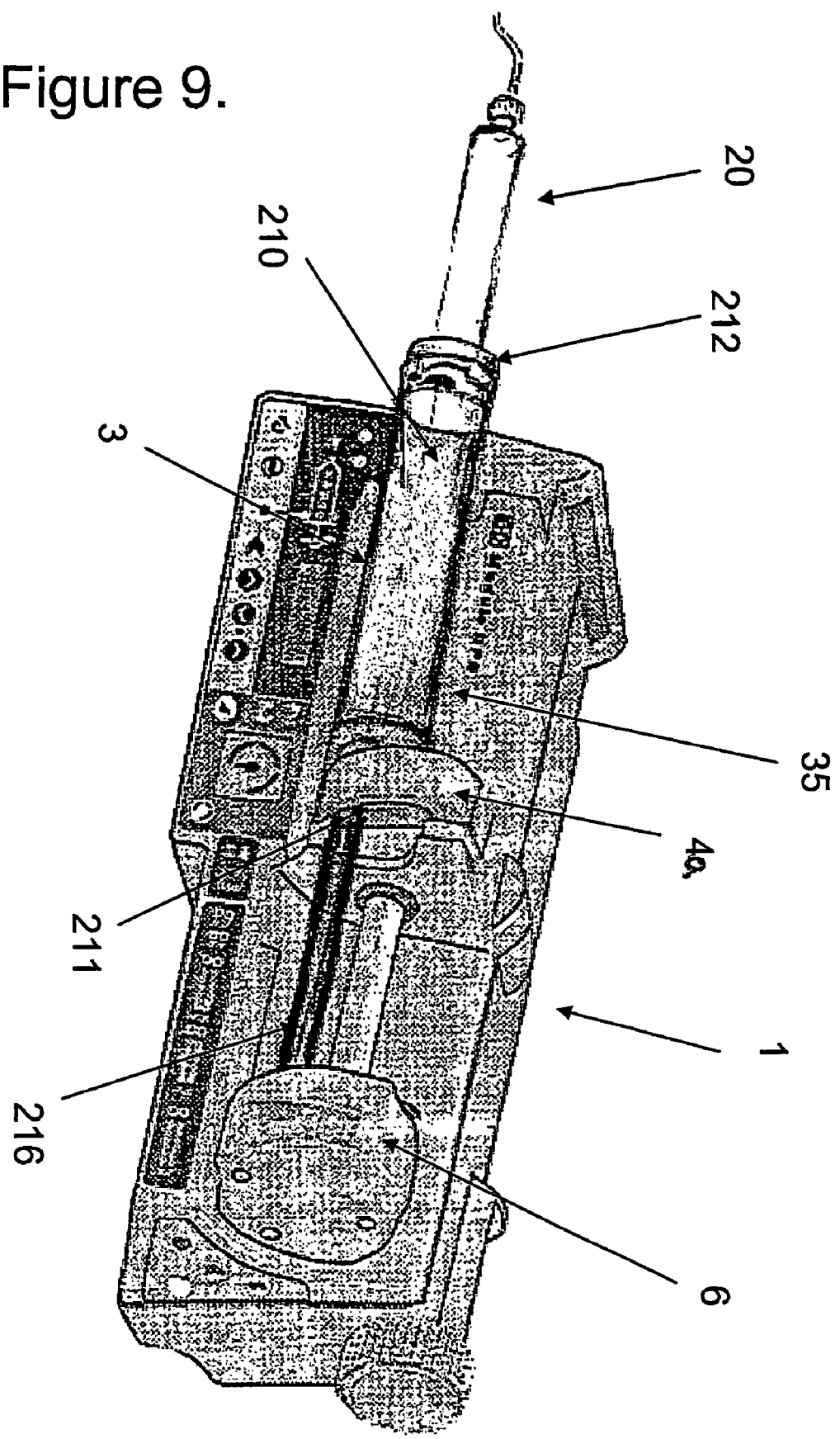
FIG. 9 illustrates the adapter of FIG. 8 placed in a pump of FIG. 1 and connected to a syringe.

FIGS. 8 and 9 illustrate another adapter 35 of the present invention, with like numerals denoting like components to the herein above described embodiments. Adapter 35 is shown connected to a syringe 20. The adapter 35 comprises an elongate substantially cylindrical housing 210, a size readable-unit 211 by which adapter 35 is retained by a pump 1, an elongate guide piston 216 and a syringe retainer 212. Syringe 20 is positioned by adapter 35 to be substantially in-line with housing 210. The housing 210 generally resembles a syringe barrel having a substantially cylindrical shape.

The adapter 35 includes a motor 256, drive shaft 258 and control circuitry, such as a battery, 262, transferring energy to the syringe ring 214 which forms a part of the syringe retainer 212.

Adapter 35 further includes an elongate guide piston 216 which is longitudinally movable under the urging of drive head 6 of pump 1. Housing 210 further defines an elongate guide piston passageway 248 for accommodating guide piston 216 therethrough. Guide piston 216 supports a syringe plunger engagement member 215 at first end 216. The member 215 is therefore able to urge the syringe plunger rod of syringe 20 towards nozzle 26 and thereby provide for dispensement of the syringe contents.

FIG. 9 illustrates an apparatus comprising the adapter 35 of FIG. 8 loaded in pump 1 and connected to a syringe 20. When adapter 35 is positioned in the syringe-receiving-unit 3 of the pump 1, clasp 4a of syringe-size-reading unit 4 is closed, thereby holding adapter 35 by the syringe-size-readable-unit 211. When having connected a syringe 20 to the syringe retainer 212 and the pump drive head 6 attaches the guide piston 216 the apparatus is ready for operation. Rate and mode of injection will be ensured by the pump, pushing the guide piston 216 at a desired rate, while the desired rotational agitation is ensured by the adapter 35.

Another embodiment of the invention is an injection apparatus employing an adapter of the present invention. Such apparatus may be used for administration of an injectable liquid and comprises an automatic syringe pump and an adapter of the invention, and optionally a syringe. Desirably, such apparatus is used for injection or infusion of a dispersion of microparticles homogeneously distributed in a carrier liquid. The adapter includes means for rotating the syringe to obtain a uniform distribution of the liquid composition in the syringe. The apparatus may further comprise a tube connected to the syringe nozzle for transferring the composition to a patient. Optionally the apparatus may comprise means for admixture of the composition of the syringe with a flushing medium prior to administration to a subject. Such means may simply comprise a three-way connector, e.g. a T-piece, a Y-piece or a tap such as a three way stopcock connected to a tubing from the syringe and a flushing medium reservoir.

Yet another embodiment of the invention is use of the adapter and the apparatus as herein described. Accordingly, a method of administering an injectable liquid composition using such apparatus is encompassed. Desirably, a method of administering is by injection or infusion of a dispersion of microparticles homogeneously distributed in a liquid carrier by an apparatus comprising a pump, a syringe comprising the dispersion and an adapter, wherein the adapter comprises means for rotating the syringe to obtain a uniform distribution in said syringe. Another aspect of this embodiment is a method of agitating a composition to be mixed or to be held homogeneous, using the adapter or the apparatus of the invention.

The adapter, method and apparatus of the invention may be used for administration of different liquid compositions to patients, human beings or animals. The compositions may be for therapeutic or diagnostic purposes. The apparatus may be used for administration of any composition comprising multi-component fluids wherein the components are not totally miscible and there is a tendency for the components to separate over time. Such composition may comprise particles that tend to settle, float, coalesce or segregate. The apparatus and method of the invention is particularly useful for administration, such as injection or infusion, of dynamic (i.e. gravity segregating) particulate dispersion systems, e.g. gas-containing diagnostic contrast agents. Examples of such ultrasound contrast agents are, for purposes of illustration and not of limitation, Levovist™, Albunex™, Optison™, Definity™, Imagent™, Sonovue™, Echogen™, Sonogen™ and Sonazoid™.

While the present invention has been discussed in connection with the delivery of a therapeutic or diagnostic liquid composition, other uses of the invention exist. The agitation mechanism provided by the adapter is also suitable for use in non-medical applications wherein mixing is desirable, such as e.g. in chemical synthesis.

While the preferred embodiment of the present invention has been shown and described, it will be obvious in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

The invention claimed is:

1. An adapter connectable with an automatic syringe pump for a hand-held syringe and a hand-held syringe, the syringe including an elongate syringe body containing contents to be dispensed, said adapter comprising
   a syringe driver for rotating the syringe body;
   an adapter body receivable by the syringe pump;
   a syringe retainer for retaining a hand-held syringe;
   an elongate guide piston, wherein said adapter body defines a guide piston opening and
   an elongate guide piston passageway in communication with said guide piston opening for slideably receiving said guide piston moving between a first and a second position;
   an extension arm supported by said guide piston, said extension arm including a free end in movable spaced registry with said syringe retainer;
   a dispense rod supported by said extension arm, said dispense rod engaging a dispensing member of the hand-held syringe so as to cause the contents to be dispensed as said dispense rod is moved relative to said syringe retainer, wherein said dispense rod is rotateably mounted to said extension arm so as to enable said dispense rod to rotate with the hand-held syringe.

2. An adapter as claimed in claim 1, wherein said adapter body is receivable by a syringe-receiving-unit of the syringe pump.

3. An adapter as claimed in claim 1, wherein said adapter body further comprises an elongate cylindrically shaped portion receivable in the syringe pump.

4. An adapter according to claim 1, wherein said syringe retainer further comprises an annular syringe ring defining an insertion aperture for engaging and retaining a hand-held syringe.

5. An adapter according to claim 4, wherein said syringe retainer engages at least one flange transversely projecting from the hand-held syringe.

6. An adapter according to claim 4, wherein said syringe driver further comprises a motor and drive means for urging said syringe ring to rotate about said insertion aperture.

7. An adapter according to claim 6, wherein said drive means further comprises a drive belt engaging a moving portion of said motor and said syringe ring.

8. An adapter according claim 4 wherein said syringe driver causes said syringe ring to reciprocally rotate about said insertion aperture.

9. An adapter as claimed in claim 1, further comprising a portion being sized and shaped so as to be recognizable by a size-reading unit of the syringe pump.

10. An adapter according to claim 1, further comprising a syringe holding arm, wherein said syringe retainer is positioned towards a free end of said syringe holding arm.

11. An adapter according to claim 1, wherein said syringe retainer is offset from said adapter body.

12. An adapter according to claim 1, wherein the adapter is adapted to connect to a hand-held syringe such that the adapter body and the hand-held syringe are positioned substantially in parallel.

13. Apparatus for administration of an injectable liquid comprising an automatic syringe pump, a syringe and an adapter as claimed in claim 1.

14. A method of administration of an injectable liquid comprising the steps of positioning a syringe in an adapter as claimed in claim 1, positioning the adapter in the place of the syringe on a syringe pump, and administering the liquid from the syringe while the adapter rotates the syringe.

* * * * *